United States Patent [19]

Treybig

[11] Patent Number: 4,676,834
[45] Date of Patent: Jun. 30, 1987

[54] NOVEL COMPOSITIONS PREPARED FROM METHYL SUBSTITUTED NITROGEN-CONTAINING AROMATIC HETEROCYCLIC COMPOUNDS AND AN ALDEHYDE OR KETONE

[75] Inventor: Duane S. Treybig, Lake Jackson, Tex.

[73] Assignee: The Dow Chemical Company, Midland, Mich.

[21] Appl. No.: 832,293

[22] Filed: Feb. 24, 1986

[51] Int. Cl.$^4$ .................................................. C04B 9/02
[52] U.S. Cl. ................................ 106/14.15; 106/14.16
[58] Field of Search ........................... 106/14.15, 14.16

[56] References Cited

U.S. PATENT DOCUMENTS

| | | | |
|---|---|---|---|
| 2,643,977 | 6/1953 | Hughes | 252/8.55 |
| 3,077,454 | 2/1963 | Monroe et al. | 252/148 |
| 3,248,334 | 4/1966 | Monroe | 252/151 |
| 3,378,488 | 4/1968 | Nimerick | 252/8.55 |
| 3,484,345 | 12/1969 | Nambride | 204/49 |
| 3,932,296 | 1/1976 | Byth | 252/148 |
| 4,100,099 | 7/1978 | Asperger et al. | 252/189 |
| 4,102,804 | 7/1978 | Clouse et al. | 252/189 |
| 4,140,640 | 2/1979 | Scherubel | 252/8.55 |
| 4,315,087 | 2/1982 | Redmore et al. | 525/421 |
| 4,339,349 | 7/1982 | Martin et al. | 252/389 A |
| 4,362,860 | 12/1982 | Ratto et al. | 528/248 |
| 4,471,107 | 9/1984 | Peake | 528/248 |
| 4,515,708 | 5/1985 | Haslegrave et al. | 252/390 |

FOREIGN PATENT DOCUMENTS 45-1265 1/1970 Japan .

OTHER PUBLICATIONS

"Pyrazine, Quinoxaline and Tetrahydroquinoxaline Derivatives" by Paul F. Wiley, *J. Am. Chem. Soc.*, 1954, vol. 76, pp. 4924–4925.
"The Mannich Reaction on 2,5-Dimethylpyrazine" by Seymour M. Linder and Paul E. Spoerri, *J. Am. Chem. Soc.*, 1952, vol. 74, pp. 1517–1518.
"The Chemistry of Pyrazine and its Derivatives, VII., the Synthesis of Vinylpyrazine and Substituted Vinylpyrazines" by Marwan R. Kamal, Mary Neubert and Robert Levine, *J. Org. Chem.*, 1962, vol. 27, pp. 1363–1366.
"Effect of 2,5-Dimethylpyrazine on Aldehydes", *Berichte der Deutschen Chemischen Gesellschaft*, vol. 38, No. 3, 1905, pp. 3724–3728.

"On α-Styrylpyridine⇌, H. Baurath, *Ber.*, 20, 1887, pp. 2719–2720.
"Condensation of α- and Y-Methylpyridine Derivatives with Cinnamaldehyde" by Spath, Kubiczek and Dubensky, *Ber.*, 74B, pp. 873–879 (1941)
"On the Condensation of α:Y:α'-Trimethylpyridine with Benzaldehyde" by Konigs and Bentheim, *Ber.*, 38, pp. 3907–3911 (1905).
"Four-Center Type Photopolymerization in Solid State" by Masaki Hasegawa in *Polymer Chem.*, vol. 27, No. 302, pp. 337–349 (1970).
"An Aldol-Type Reaction of Active Methyl Groups of Nitrogen-Containing Heteroaromatic Compounds" by Hiroshi Hamana and Tsutomu Sugasawa in *Chemistry Letters*, vol. 3, pp. 333–336 (1983).
"The Chemistry of Pyrazine and its Derivatives, XI, the Participation of Tetramethylpyrazine in Alkylation and Aldol-Type Reactions" by S. K. Chakrabartty and R. Levine in *J. Heterocyclic Chem.*, vol. 3, pp. 265–268 (1966).
"Chemistry of Pyrazine and its Derivatives, III, the Synthesis of Carbinols by the Participation of Methylpyrazine in Aldol-Type Condensations" by J. D. Behun and R. Levine in *J. Amer. Chem. Soc.*, vol. 81, pp. 5666–5669 (1959).
*Chem. Abstr.* 89:163549n "The Preparation of 1-(-diazinyl)-2-(Pyridyl)Ethenes (Triazastilbenes)" by H. Felbecker, D. Hollenberg, R. Schaaf, T. Bluhm and H. H. Perkampus, *J. Heterocycl. Chem.*, vol. 15, pp. 749–752 (1978).
*Chem. Abstr.* 86:120240a "Synthesis and Spectral Properties of 1,2-Bispyrazyl Ethylene" by S. C. Shim, D. S. Lee, J. S. Chae and P. Song, Taehan Hwahak Hoechi., vol. 20, pp. 398–405 (1976).
*Chem. Abstr.* 69:92421p (French Pat. No. 1,497,474 Published Oct. 13, 1967).

*Primary Examiner*—Amelia B. Yarbrough
*Attorney, Agent, or Firm*—James G. Carter

[57] ABSTRACT

Novel compositions are prepared by reacting methyl substituted nitrogen-containing aromatic heterocyclic compounds such as 2,5-dimethylpyrazine or 2,4,6-trimethylpyridine and an aldehyde such as 1-dodecanal or ketone such as 5,7-dimethyl-3,5,9-decatrien-2-one in the presence of a suitable catalyst such as zinc chloride. These novel compositions are useful as oil and gas well corrosion inhibitors.

37 Claims, No Drawings

NOVEL COMPOSITIONS PREPARED FROM METHYL SUBSTITUTED NITROGEN-CONTAINING AROMATIC HETEROCYCLIC COMPOUNDS AND AN ALDEHYDE OR KETONE

BACKGROUND OF THE INVENTION

The present invention pertains to novel compositions prepared by reacting methyl substituted nitrogen-containing aromatic heterocyclic compounds with aldehydes or ketones.

During the drilling and servicing of oil and gas wells, the metal tools and equipment associated therewith are susceptible to corrosion. It is therefore highly desirable to have corrosion inhibitors for the protection of these metal tools and equipment. The present invention provides corrosion inhibitors for metals for use at both low and high temperatures.

SUMMARY OF THE INVENTION

One aspect of the present invention concerns new compositions of matter which comprises the product resulting from reacting
(A) at least one aromatic heterocyclic material except pyridine or quinoline having one or more rings, at least two nitrogen atoms and at least one substituent group which has at least one reactive hydrogen atom attached to a carbon atom which is attached to an aromatic heterocyclic ring; and
(B) at least one saturated or unsaturated aliphatic or cycloaliphatic monoaldehyde having at least six carbon atoms; and
wherein components (A) and (B) are employed in a molar ratio of (A) to (B) of from about 0.2:1 to about 5:1, preferably from about 0.75:1 to about 1.5:1.

Another aspect of the present invention concerns new compositions of matter which comprises the product resulting from reacting
(A) at least one aromatic heterocyclic material having one or more rings, at least one nitrogen atom and at least one substituent group which has at least one reactive hydrogen atom attached to a carbon atom which is attached to an aromatic heterocyclic ring; and
(B) at least one saturated or unsaturated aliphatic or cycloaliphatic ketone or mixture of aldehyde and ketone having at least six carbon atoms; and
wherein components (A) and (B) are employed in a molar ratio of (A) to (B) of from about 0.2:1 to about 5:1, preferably from about 0.75:1 to about 1.5:1.

Another aspect of the present invention pertains to a process for preventing or reducing the corrosion of a metal composition in contact with corrosive fluids which process comprises contacting the surface of said metal composition with an effective amount of the aforementioned corrosion inhibitor composition.

Another aspect of the present invention pertains to a process for preventing or reducing the corrosion of a metal composition in contact with down hole well fluids, which process comprises contacting the surface of said metal composition with an effective amount of a composition which comprises the reaction product of
(A) at least one pyridine or quinoline having at least one substituent group which has at least one reactive hydrogen atom attached to a carbon atom which is attached to the pyridine or quinoline ring; and
(B) at least one saturated or unsaturated aliphatic or cycloaliphatic monoaldehyde; and
wherein components (A) and (B) are employed in a molar ratio of (A) to (B) of from about 0.2:1 to about 5:1, preferably from about 0.75:1 to about 1.5:1.

Another aspect of the present invention pertains to a process for preventing or reducing the corrosion of a metal composition in contact with down hole well fluids, which process comprises contacting the surface of said metal composition with an effective amount of a composition which comprises the reaction product of
(A) at least one aromatic heterocyclic material having one or more rings, at least one nitrogen atom and at least one substituent group which has at least one reactive hydrogen atom attached to a carbon atom which is attached to an aromatic heterocyclic ring; and
(B) at least one aromatic, aryl substituted aliphatic or aliphatic substituted aromatic monoaldehyde, ketone or their mixture; and
wherein components (A) and (B) are employed in a molar ratio of (A) to (B) of from about 0.2:1 to about 5:1, preferably from about 0.75:1 to about 1.5:1.

Another aspect of the present invention pertains to a corrosion inhibitor composition comprising (A) a carrier liquid and (B) a corrosion inhibitor which is the product which results from reacting (1) at least one material having one or more rings, at least one nitrogen atom and at least one substituent group which has at least one reactive hydrogen atom which is attached to a carbon atom which is attached to a heterocyclic ring with (2) a monoaldehyde, ketone or mixture of monoaldehyde or ketone.

DETAILED DESCRIPTION OF THE INVENTION

The compositions of this invention are preferably prepared by reacting a monoaldehyde, ketone or mixture of monoaldehyde and ketone with an alkyl substituted nitrogen-containing aromatic heterocyclic compound. Preferably, the reaction is carried out in an inert atmosphere or under reduced pressure. It is also desirable to conduct the reaction in the presence of a catalyst. The reaction can be carried out neat or in the presence of a solvent. The reaction is carried out at a temperature between about 25° to about 250° C., preferably from 120° to 200° C. for about 1-72 hours (3600-259,200 s), especially 12-60 hours (43,200-216,000 s).

Examples of an inert atmosphere in which the reaction can be conducted includes nitrogen, helium, neon, xenon, argon mixtures thereof and the like.

Suitable catalysts which can be employed include, for example, acids, Lewis acids, bases or salts. Particularly suitable acids include, for example, sulfuric, hydrochloric or p-toluene-sulfonic acid. Particularly suitable bases include, for example, hydroxides of alkali or alkaline earth metals or of quaternary ammonium, n-butyllithium, phenyllithium or sodium amide in liquid ammonia. Particularly suitable Lewis acids include, for example, boron trifluoride and the like. Particularly suitable salts include, for example, zinc chloride or aluminum chloride. The use of such catalysts is not indispensable but it reduces the time required for the reaction. The amount is e.g. of from about 0.1 to about 10 mole% with respect to the aldehyde or ketone. If desirable, larger or lesser quantities can be employed.

The reaction can also be accelerated by certain substances such as methyl iodide, methyl sulfate, benzyl chloride etc., capable of forming with the pyridinic and/or pyrazinic base quaternary ammonium derivatives, such substances being usable in catalytic amounts or higher proportions.

Dehydrating agents such as acetic anhydride, trifluoroacetic anhydride, propionic anhydride and the like can promote the reactions and its action can be sufficient to render superfluous the incorporation of a catalyst. The amount of anhydride used ranges from 1 to 10, preferably 1.1 to 5 moles per mole of aldehyde or ketone. The preferred dehydrating medium is a mixture of glacial acetic acid and acetic anhydride. The acetic acid and acetic anhydride can be removed by distillation, solvent extraction, solvent fractionation or by neutralization with a base. Examples of several solvent fractionation methods are described in U.S. Pat. Nos. 4,362,860 and 4,471,107 which are incorporated herein by reference. Suitable bases include sodium hydroxide, ammonia hydroxide and ammonia.

Suitable solvents include, any solvents in which the reactants and products are soluble such as alcohols, chlorinated solvents, ketone, acids, amides, ethers, aromatic heterocycles containing no alkyl substituents and hydrocarbons. Particularly suitable solvents include, for example, ethanol, isopropanol, methylene chloride, glacial acetic acid, dioxane, tetrahydrofuran, dimethylformamide, N,N-dimethylacetamide, N,N-dimethylmethoxyacetamide, N-methylpyrrolidinone, pyridine, toluene, xylene, combinations thereof and the like.

Suitable aromatic heterocyclic materials having one or more rings, at least one nitrogen atom and at least one substituent group which has at least one reactive hydrogen atom attached to a carbon atom which is attached to an aromatic heterocyclic ring which can be employed herein include, for example, pyrazines, pyridines, pyrazoles, imidazoles, pyridazines, pyrimidines, purines, pteridines, triazines, quinolines and quinoxalines. Particularly suitable such substituent groups include methyl, —CH(R)$_2$ or —CH$_2$R groups wherein each R is independently a hydrocarbyl group containing from 1 to about 20, preferably 1 carbon atom.

The term hydrocarbyl as employed herein means any aliphatic, cycloaliphatic, aromatic, aryl substituted aliphatic or aliphatic substituted aromatic groups.

Particularly suitable as the heterocyclic material which can be employed herein include the pyrazines such as, for example, 2-methylpyrazine, 2,3-dimethylpyrazine, 2,5-dimethylpyrazine, 2,6-dimethylpyrazine, 2,3,5-trimethylpyrazine, 2,3,5,6-tetramethylpyrazine, 2-ethylpyrazine, 2-ethyl-3-methylpyrazine, 2-ethyl-5-methylpyrazine, 2-ethyl-6-methylpyrazine, 2-ethyl-3,5-dimethylpyrazine, 3-ethyl-2,5-dimethylpyrazine, 5-ethyl-2,3-dimethylpyrazine, 2-propylpyrazine, 2-methyl-3-propylpyrazine, 2-methyl-6-propylpyrazine, 2,5-dimethyl-3-propylpyrazine, 3,5-dimethyl-2-propylpyrazine, 2-(1-methylethyl)pyrazine, 2-methyl-3-(1-methylethyl)pyrazine, 2-methyl-5-(1-methylethyl)pyrazine, 6-methyl-2-(1-methylethyl)pyrazine, 2,3-diethylpyrazine, 2,3-diethyl-5-methylpyrazine, 3,5-diethyl-2-methylpyrazine, 2,6-diethyl-3,5-dimethylpyrazine, 2,5-diethyl-3,6-dimethylpyrazine, 2,5-bis(1-methylethyl)pyrazine, 2,5-dimethyl-3,6-bis(1-methylethyl)pyrazine, 2-butylpyrazine, 2-butyl-3-methylpyrazine, 2-butyl-6-methylpyrazine, 2-butyl-3,5-dimethylpyrazine, 3-butyl-2,5-dimethylpyrazine, 5-butyl-2,3-dimethylpyrazine, 2-butyl-3,5,6-trimethylpyrazine, 2,5-dibutyl-3,6-dimethylpyrazine, 2,5-dimethyl-3,6-bis(2-methylpropyl)pyrazine, 2,5-diethyl-3,6-bis(2-methylpropyl)pyrazine, 2-methyl-3-(2-methylpropyl)pyrazine, 2,3,5-trimethyl-6-(2-methylpropyl)pyrazine, 2-methyl-3-pentylpyrazine, 2-hexylpyrazine, 2-hexyl-3-methylpyrazine, 2,5-dimethyl-3,6-pyrazinediamine, 2,3,5-trimethyl-6-nitropyrazine, 2-chloro-3,5-dimethylpyrazine, mixtures thereof and the like.

Particularly suitable pyridines which can be employed herein include, for example, 2-methylpyridine, 4-methylpyridine, 2,3-dimethylpyridine, 2,4-dimethylpyridine, 2,5-dimethylpyridine, 2,6-dimethylpyridine, 2-ethylpyridine, 2,3,4-trimethylpyridine, 2,3,5-trimethylpyridine, 2,3,6-trimethylpyridine, 2,4,5-trimethylpyridine, 2,4,6-trimethylpyridine, 2-ethyl-3-methylpyridine, 2-ethyl-4-methylpyridine, 3-ethyl-2-methylpyridine, 3-ethyl-4-methylpyridine, 2-ethyl-6-methylpyridine, 5-ethyl-2-methylpyridine, 4-ethyl-2-methylpyridine, 2,4-diethylpyridine, 3,6-diethyl-2-methylpyridine, 2-ethyl-3,6-dimethylpyridine, 3-ethyl-2,6-dimethylpyridine, 4-ethyl-2,5-dimethylpyridine, 2-ethyl-4,6-dimethylpyridine, 2-methyl-4-propylpyridine, 2-methyl-4-(1-methylethyl)pyridine, 2-(1,1-dimethylethyl)-4-methylpyridine, 4-(1,1-dimethylethyl)-2-methylpyridine, 2,3-dimethyl-6-(1-methylethyl)pyridine, 3,6-dimethyl-2-(1-methylethyl)pyridine, 2,6-dimethyl-4-propylpyridine, 3,6-dimethyl-2-propylpyridine, 2-ethyl-3,4,6-trimethylpyridine, 3-ethyl-2,5,6-trimethylpyridine, 2-methyl-4-(1-methylpropyl)pyridine, 4-butyl-2-methylpyridine, 5-butyl-2-methylpyridine, 2,3,4,5-tetramethylpyridine, 2,3,4,6-tetramethylpyridine, 2,3,5,6-tetramethylpyridine, pentamethylpyridine, mixtures thereof and the like.

Other suitable aromatic nitrogen containing heterocycles which can be employed herein include, pyrazoles, imidazoles, pyridazines, pyrimidines, purines, pteridines, triazines, quinolines and quinoxalines having one or more substituents having a reactive hydrogen atom attached to a carbon atom which is attached to the heterocyclic ring. Such substituent groups include methyl, —CH(R)$_2$ or —CH$_2$R wherein R is as above defined.

Suitable pyrazoles include 3-methylpyrazole, 3,5-dimethylpyrazole, 1-ethyl-3,5-dimethylpyrazole, 3,4,5-trimethylpyrazole, mixtures thereof and the like.

Suitable imidazoles which can be employed herein include, for example, 2-methylimidazole, 4-methylimidazole, 1,2-dimethylimidazole, 2,5-dimethylimidazole, 2,4-dimethylimidazole, 2,4,5-trimethylimidazole, 2-ethyl-4-methylimidazole, mixtures thereof and the like.

Suitable pyridazines include, for example, 3-methylpyridazine, 3,5-dimethylpyridazine, 3,4,5-trimethylpyridazine, mixtures thereof and the like.

Suitable pyrimidines include, for example, 4-methylpyrimidine, 2,4-dimethylpyrimidine, 4,5-dimethylpyrimidine, 4,6-dimethylpyrimidine, 2,6-dimethyl-4-pyridinamine, 2,6-dimethyl-4-pyrimidinol, 2,4-dichloro-6-methylpyrimidine, 2,4,6-trimethylpyrimidine, 2,4-diethylpyrimidine, mixtures thereof and the like.

Suitable purines which can be employed herein include, for example, 6-methylpurine, 2,8-dimethylpurine, 2,8-dimethyl-6-purinamine, 2,6,8-trimethylpurine, mixtures thereof and the like.

Suitable pteridines include 6,7-dimethylpteridine, 2,6-dimethylpteridine, 2,4,7-trimethylpteridine, mixtures thereof and the like.

Suitable triazines which can be employed herein include 3,5-dimethyl-1,2,4-triazine, 3,6-dimethyl-1,2,4- triazine, 2,4-dimethyl-1,3,5-triazine, 2,4,6-trimethyl-1,3,5-triazine, mixtures thereof and the like.

Suitable quinolines include, for example, 2-methylquinoline, 4-methylquinoline, 2,4-dimethylquinoline, 2,6-dimethylquinoline, 2,7-dimethylquinoline, 8-ethyl-2-methylquinoline, 4-ethyl-2,3-dimethylquinoline, 8-ethyl-2,3-dimethylquinoline, 4-ethyl-2,3,8-trimethylquinoline, 4,8-diethyl-2,3-dimethylquinoline, 2,3-dimethyl-8-propylquinoline, 2,3,4-trimethyl-8-propylquinoline, 2,4-dimethyl-6-(1-methylpropyl)quinoline, mixtures thereof and the like.

Suitable quinoxalines include 2-methylquinoxaline, 2,5-dimethylquinoxaline, 2,3-dimethylquinoxaline, 2,6-dimethylquinoxaline, 2,3,6-trimethylquinoxaline, 2,3,6,8-tetramethylquinoxaline, mixtures thereof and the like.

The aromatic heterocyclic materials having one or more rings and at least one nitrogen atom and at least one substituent group which has at least one reactive hydrogen atom attached to a carbon atom which is attached to an aromatic heterocyclic ring can be mixed with each other. For example, 5-ethyl-2-methylpyridine can be mixed with 2-ethyl-3,5-dimethylpyrazine and used as the heterocyclic material in the present invention.

In the preparation of the new compositions of matter of the present invention any monoaldehyde except those with less than a total of 6 carbon atoms and aromatic aldehydes is suitable. Particularly suitable are those represented by the following formulas

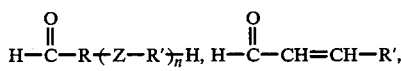

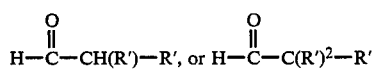

wherein R is a divalent saturated or unsaturated aliphatic or cycloaliphatic group or halogen, nitro, hydroxyl or thiol substituted divalent saturated or unsaturated aliphatic or cycloaliphatic group, R' is a hydrocarbyl group, Z is oxygen or sulfur and n has a value of zero or 1 and said monoaldehyde has from 6 to about 72, preferably from about 10 to about 36, most preferably from about 12 to about 24 carbon atoms.

In the preparation of the reaction products which can be employed as corrosion inhibitors any monoaldehyde can be employed, even the aromatic aldehydes.

Suitable such aldehydes, include, butanal, pentanal, hexanal, octanal, nonanal, decanal, undecanal, 2-methylundecanal, 2,6,10-trimethylundecanal, acrolein, 2-butenal (crotonaldehyde), trans-2-hexenal, trans,trans-2,4-hexadienal, trans-2-heptenal, 2,4-dimethyl-2,6-heptadienal, 2,4-diethyl-2,6-heptadienal, Citral, 1-Citronellal, 2-nonenal, 3-nonenal, 4-nonenal, 7-nonenal, 2,3-nonadienal, 2,4-nonadienal, 4,7-nonadienal, undecenal, 4-(1-methylethenyl)-1-cyclohexene-1-carboxyaldehyde (Perillaldehyde), trans-Retinal, benzaldehyde, 4-butoxybenzaldehyde, 4-(methylthio)benzaldehyde, 3-pehnyl-2-propenal (trans-cinnamaldehyde), 2-chloro-3-phenyl-2-propenal, 3-(2-nitrophenyl)-2-propenal, 3,3-diphenyl-2-propenal, 2-pyrenecarboxaldehyde, 9H-fluorene-2-carboxaldehyde, mixtures thereof and the like.

Particularly suitable aldehydes include, dodecanal (dodecyl aldehyde), tridecanal, 12-methyltridecanal, tetradecanal (myristyl aldehyde), 2,6-dimethyltetradecanal, 5,9,13-trimethyl-2-(1-methylethyl)tetradecanal, 2-pentyldecanal, 4,8,12-trimethylpentadecanedial, hexadecanal, hexadecanedial, 3,7,11,15-tetramethylhexadecanal, heptadecanal, octadecanal, octadecanedial, nonadecanal, eicosanal, heneicosanal, cis-7-tetradecenal, 2-pentadecenal, 10-pentadecenal, 2-hexadecenal, 11-hexadecenal, 11-octadecenal, 13-octadecenal, 2,4-octadecadienal, 3,6-octadecadienal, 9,12-octadecadienal, 6,9,12-octadecatrienal, 9,12,15-octadecatrienal, 2-eicosenal, mixtures thereof and the like.

Thermal stability and film forming tenacity of a corrosion inhibitor is usually improved to some degree from crosslinking of the reactants. Polyaldehydes can be mixed with monoaldehydes to crosslink the reactants. Another necessary criteria for crosslinking the reactants is the presence of an aromatic heterocyclic compound having alkyl substituents with at least two reactive hydrogen atoms. Suitable polyaldehydes which can be mixed with the above monoaldehydes to crosslink the reactants include, ethanedial (glyoxal), propanedial (pyruvic aldehyde), pentanedial (glutaric dialdehyde), 1,4-benzenedicarboxaldehyde (terephthaldicarboxaldehyde), 1,2-benzenedicarboxaldehyde, mixtures thereof and the like.

In the preparation of the new compositions of matter of the present invention any monoketone except those with less than a total of 6 carbon atoms and with an aromatic group is suitable.

In the preparation of the reaction products which can be employed as corrosion inhibitors any monoketone can be employed, even the aromatic ketones.

Suitable such ketones include, 2-heptanone, 2-nonanone, 3-nonanone, 2-decanone, 2-undecanone, 8-pentadecanone, 7-octadecanone, 1-phenyl-2-butanone, 4-phenyl-2-butanone, 1-(4-methoxyphenyl)-2-propanone, 1-(4-methoxyphenyl)-1-propanone, 1-(4-fluorophenyl)-2-propanone, 1,3-diphenyl-2-propanone, mixtures thereof and the like.

Particularly suitable ketones include, 5,7-dimethyl-3,5,9-decatrien-2-one, 1-phenyl-1-dodecanone, 1-(3-methoxyphenyl)-1-octadecanone, 2-pentadecanone, 6,10,14-trimethyl-3,5-pentadecadien-2-one, 6,10,14-trimethyl-4,5-pentadecadien-2-one, 6,10,14-trimethyl-3,5,9-pentadecatrien-2-one, 2-octadecanone, 7-octadecanone, octadecen-5-one, 2-nonadecanone, 3-nonadecanone, 10-nonadecen-2-one, 8-nonadecan-7-one, 7,10,13-nonadecatrien-2-one, 10,13,16-nonadecatrien-2-one, 2-eicosanone, 3-eicosanone, 1-eicosen-3-one, 11-eicosen-3one, mixtures thereof and the like.

Polyketones can be mixed with monoketones to crosslink the reactants to improve thermal stability and film forming tenacity of the corrosion inhibitor. Suitable polyketones which can be mixed with the above monoketones to crosslink the reactants include, 2,4-pentanedione, 2,5-hexanedione, mixtures thereof and the like.

The compositions of the present invention can be employed as a corrosion inhibitor as are conventional corrosion inhibitors. Generally, the product can be employed in corrosion inhibitor formulations as are known in the art. For example, the product can be dispersed or dissolved in a suitable carrier liquid or solvent such as water, alcohols, aromatic and aliphatic hydrocarbons, and the like, or mixtures thereof. Other additives include demulsifiers, water wetting agents, surfactants, viscosifiers, commingled gases, defoamers, other corrosion inhibitors such as polymeric materials and salts, organic and inorganic acids, iron control agents, sequestering and/or chelating agents, phosphates, quaternaries, amine salts, and the like. For example, surface active agents are used to assure complete dispersion of active ingredients throughout the corrosion inhibitor composition and thus provide a better contact of the corrosion inhibitor with the surface of the metal compound which is being protected.

The corrosion inhibitor of this invention is employed in a functionally effective amount. That is, any quantity of corrosion inhibitor which will provide some degree of inhibition of corrosion is sufficient. Typical amounts of corrosion inhibitor which are employed in an oil and/or gas well treatment can range from about 5 to about 2,000 ppm for continuous treatment or about 1,000 to about 50,000 ppm for squeeze treatment, based on the weight of corrosive well fluids in contact with the metal compositions which are protected. Amounts of corrosion inhibitor in excess of 50,000 ppm can provide additional corrosion inhibition but at increased expense.

The corrosion inhibitors of this invention are stable to high temperatures and high pressures. Typically, corrosion inhibitors for oil and gas wells are employed in applications where temperatures range from about 100° F. (37.7° C.) to in excess of about 500° F. (260° C.), depending upon the composition of the product. The corrosion inhibitors of this invention are especially useful at temperatures ranging from 300° F. (148.8° C.) to about 356° F. (180° C.). Useful applications include oil and/or gas well drilling, completion, workover, stimulation, transfer, processing and storage applications.

The following examples are illustrative of the present invention.

CORROSION TESTING, 175° F. (79.4° C.)

Corrosion inhibition of various samples was determined under conditions which simulate conditions that exist in oil and gas wells as follows. A brine solution containing 89.89 percent deionized water, 9.62 percent sodium chloride, 0.305 percent calcium chloride and a 0.186 percent hydrated magnesium chloride complex was prepared. This brine solution was purged with carbon dioxide until a pH of 3.8 was achieved. The solution was treated with sodium persulfate to remove oxygen. The desired corrosion inhibitor was added to the solution. About 720 milliliters (ml) of this brine solution and 80 ml of kerosene (90% brine/10% kerosene) treated with sodium persulfate were charged into a 32-ounce bottle. To this charge was added enough hydrated sodium sulfide to generate a suitable amount of hydrogen sulfide (i.e., about 300 ppm hydrogen sulfide based on total fluids).

Metal coupons (12"×¼"×1/16", 304.8 mm×6.35 mm×1.59 mm) of 1020 carbon steel were degreased with an inhibited methylchloroform, acidized with 16 percent hydrochloric acid, washed and dried. Each coupon weighed about 19 g. A metal coupon was placed in the bottle containing the brine, kerosene and ingredients as previously described. The bottle was capped and acetic acid was injected into the bottle through a septum. The bottle was placed on a vertically rotating wheel held at 175° F. (79.4° C.) and the sample was rotated at 26 rpm for 24 hours (86,400 s). The coupons were removed from the bottle, cleaned, washed, dried, reweighed and the percent protection afforded them by the inhibitor was calculated by the following formula:

$$\text{percent protection} = 100 - \frac{\text{inhibitor coupon wt. loss}}{\text{blank coupon wt. loss}} \times 100$$

The weight loss was given to the nearest whole percent. The tests wherein no inhibitor was employed are for comparative purposes and are designated as blanks.

The corrosion rates were also determined in milliinches per year (mpy) by the following formula:

$$mpy = \frac{534 \text{ (Mg Weight Loss of Coupon)}}{d \times a \times t}$$

d = density of 1020 carbon steel = 7.86 g/ml
a = surface area (in.) of metal coupons
t = test time in hours

CORROSION TESTING, 350° F. (177° C.)

The performance of 100 ppm of a corrosion inhibitor sample also was tested in a 350° F. (177° C.) wheel test containing 90 percent brine/8 percent heptane/2 percent kerosene at 2,000 psi pressure (25° C.) with 10 percent hydrogen sulfide, 10 percent carbon dioxide and 80 percent methane in a stainless steel pipe bomb. The sample was rotated at 26 rpm for 24 hours (86,400 s). Metal coupons (6"×¼"×1/16", 152.4 mm×6.35 mm×1.59 mm) of 1020 carbon steel were degreased with chlorothene, scrubbed, washed with acetone and dried before being placed in the pipe bomb. After the test, the coupons were removed from the pipe bomb, scrubbed, washed with acetone and dried. Percent protection was calculated using the same equations as in the above 175° F. corrosion test.

EXAMPLE 1

2,5-Dimethylpyrazine (105 g, 0.97 mole) and 1-dodecanal (267 g, 1.45 moles) were stirred in a 500 ml resin kettle equipped with an immersion thermometer, mechanical stirrer, condenser, Barrett trap and nitrogen inlet tube. After complete dissolution, zinc chloride (4.72 g, 0.035 mole) was added to the reactor. The reactants were heated between 84°–185° C. for 22 hours 48 minutes (82,080 s) giving a dark reddish brown liquid. Fifty-three percent of the liquid (8.6 ml) caught in the Barrett trap was water. The infrared spectrum of the dark reddish brown liquid showed absorption bands at 1690 cm$^{-1}$ and 1740 cm$^{-1}$ which were assigned to carbonyl and —C═C— groups. The infrared results suggest the self-condensation product of 1-dodecanal is the primary reaction product. The reaction product consisted of 1.5% nitrogen, 79.1% carbon, 5.4% oxygen and 14% hydrogen according to CHN analysis. A small concentration of the following fatty styrylpyrazine,

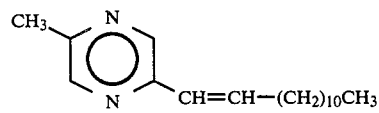

and a large concentration of the self-condensation product of 1-dodecanal,

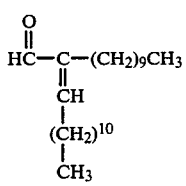

were identified by electron impact capillary mass spectroscopy.

EXAMPLE 2

2,4,6-Trimethylpyridine (40.4 g, 0.33 mole) and zinc chloride (6.45 g, 0.047 mole) were stirred at 135° C. in a 1-liter resin kettle equipped with an immersion thermometer, mechanical stirrer, condenser, addition flask and nitrogen inlet tube. 50 wt./wt.% solution of 1-dodecanal (204.4 g, 1.11 moles) in heptanol (202.8 g, 1.75 moles) was added dropwise to the reactor contents over a period of 9 hours 15 minutes (33,300 s). The reactor contents were then heated between 150°-210° C. for 3 hours 15 minutes (11,700 s). The reactor contents were cooled to room temperature, and rotary evaporated at 100° C. and 6 mm mercury (Hg) vacuum. The condensation product of 1-heptanal with 2,4,6-trimethylpyridine,

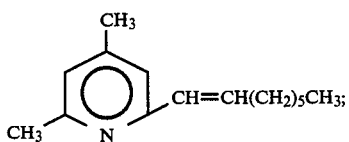

the condensation product of 1-dodecanal with 2,4,6-trimethylpyridine,

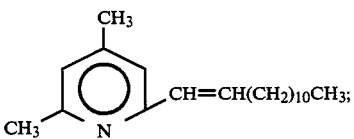

the condensation product of two molecules of 1-dodecanal with 2,4,6-trimethylpyridine and 1-dodecanal condensed with itself were identified with electron impact capillary mass spectroscopy. The mass of the condensation product of three molecules of 1-dodecanal and 2,4,6-trimethylpyridine,

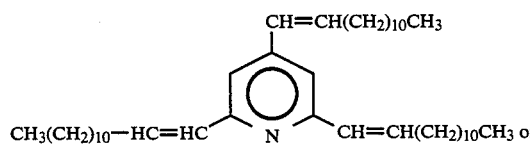

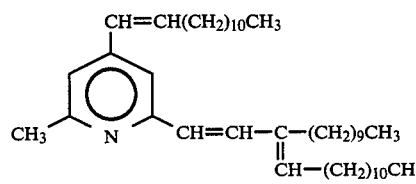

was identified by using methane chemical ionization probe mass spectroscopy.

EXAMPLE 3

2,4,6-Trimethylpyridine (83.6 grams, 0.69 mole) and dodecanal (185.56 grams, 1 mole) were weighed into a reactor of the type described in Example 1. After complete dissolution, 3.46 grams of zinc chloride (0.025 mole) was added to the reactor. The reactor contents were heated between 140°-167° C. for 49 hours 3 minutes (176,580 s) while being stirred in a nitrogen atmosphere. Then the reactor was fitted with a still head and its contents were subjected to distillation between 170°-204° C. and 151-162 mm mercury vacuum for 4 hours 22 minutes (15,720 s). The reactor contents were cooled to room temperature giving a dark brown liquid. The dark brown liquid was soluble in xylene.

EXAMPLE 4

2,3,5,6-Tetramethylpyrazine (74 g, 0.54 mole) and 2-methylundecanal (97 g, 0.53 mole) were stirred in a reactor of the type described in Example 1. After complete dissolution, concentrated sulfuric acid (1.98 g, 0.02 mole) was added to the reactor. Concentrated sulfuric acid (1.44 g, 0.015 mole) was again added to the reactor contents after heating between 139°-215° C. for 3 hours 57 minutes (14,220 s). The reactor contents were heated for an additional 18 hours 34 minutes (66,840 s) between 128°-203° C. The black colored reaction product was rotary evaporated at 100° C. and 20 mm Hg vacuum and subjected to extraction with water to remove unreacted tetramethylpyrazine. After distillation with a Vigreaux column at 183° C. bottoms temperature and 17 mm Hg vacuum, the distillation bottoms consisted of 17 area% 2-methylundecanal, 18 area% of the methylester of undecanoic acid and 54 area% of various reaction products according to a gas chromatographic analysis. Four isomers of the condensation product of tetramethylpyrazine and 2-methylundecanal,

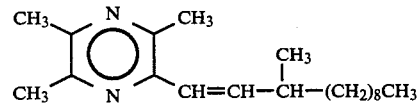

were identified as the major reaction products by electron impact capillary mass spectroscopy.

EXAMPLE 5

The distilled reaction product of Example 4 was distilled further at a 250° C. bottoms temperature and 17 mm Hg vacuum. The distillation bottoms consisted of 17 area% methyl ester of undecanoic acid and 78.7 area% of various reaction products according to a gas chromatographic analysis. The condensation product of two molecules of 2-methylundecanal with tetramethylpyrazine,

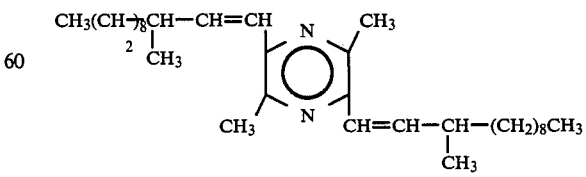

was identified in addition to the fatty styrylpyrazine isomers found in Example 4 by electron impact capillary mass spectroscopy. Differential scanning calorimetry indicated isomerization or decomposition of the distillation bottoms from the reaction of 2,3,5,6-tetramethylpyrazine with 2-methylundecanal, occurred at or above 240° C.

EXAMPLE 6

2,3,5,6-Tetramethylpyrazine (121 g, 0.89 mole), trans, trans-2,4-nonadienal (73 g, 0.53 mole) and glacial acetic acid (65 g, 1.08 moles) were weighed into a reactor of the type described in Example 1. After the reactants were deoxygenated by stirring between 72°–103° C. for 21 minutes (1260 s) in a nitrogen atmosphere, acetic anhydride (111 g, 109 moles) was added to the reactor contents. The reactor contents were heated between 122°–149° C. for 51 hours 4 minutes (183,840 s) giving a reddish brown colored liquid. The reactor contents were heated between 150°–180° C. for an additional 24 hours 2 minutes (86,520 s) giving a viscous black colored liquid. Electron impact capillary mass spectroscopy showed the reactor contents consisted primarily of isomers of the condensation product of tetramethylpyrazine and trans, trans-2,4-nonadienal,

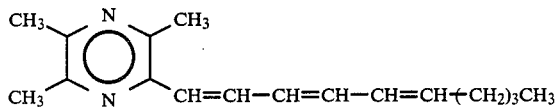

and unreacted tetramethylpyrazine. The tetramethylpyrazine was removed by extraction with water followed by vacuum distillation.

EXAMPLE 7

2,5-Dimethylpyrazine (33.6 grams, 0.31 mole), tetradecanal (98.99 grams, 0.47 mole) and zinc chloride (1.61 grams, 0.012 mole) were weighted into a reactor of the type described in Example 1. The reactor contents were heated between 138°–168° C. for 55 hours 22 minutes (199,320 s) giving a dark brown liquid. The dark brown liquid was soluble in xylene.

EXAMPLE 8

2,5-Dimethylpyrazine (101.1 grams, 0.93 mole), trans-cinnamaldehyde (122.1 grams, 0.92 mole) and zinc chloride (3.16 grams, 0.023 mole) were weighed into a reactor of the type described in Example 1. The reactor contents were heated between 133–156° C. for 25 hours 29 minutes (92,740 s) while being stirred in a nitrogen atmosphere.

EXAMPLE 9

2,5-Dimethylpyrazine (40.7 grams, 0.38 mole), 5,7-dimethyl-3,5,9-decatrien-2-one (99.48 grams, 0.56 mole) and zinc chloride (1.91 grams, 0.014 mole) were weighed into a 4-neck 250 ml round bottom flask equipped with a mechanical stirrer, immersion thermometer, condenser and nitrogen inlet tube. The reactor contents were heated between 143°–161° C. for 19 hours 12 minutes (69,120 s). The reactor contents were cooled to room temperature giving a brown liquid. The brown liquid was soluble in ethanol and xylene.

EXAMPLE 10

2,5-Dimethylpyrazine (107.1 grams, 0.99 mole), 2-undecanone (249.1 grams, 1.46 moles) and zinc chloride (5.23 grams, 0.038 mole) were weighed into a reactor of the type described in Example 1. The reactor contents were heated between 142°–198° C. for 47 hours 53 minutes (172,380 s) while being stirred in a nitrogen atmosphere. Then the reactor was fitted with a still head and its contents were subjected to distillation between 149°–210° C. and 45–117 mm mercury vacuum for 46 minutes (2760 s). The reactor contents were cooled to room temperature giving a dark brown liquid. The dark brown liquid was soluble in xylene and ethanol.

EXAMPLE 11

This example demonstrates the corrosion protection of the inhibitors of this invention by the 175° F. batch wheel test procedure.

TABLE I

| | 80° Wheel Test | | | | |
|---|---|---|---|---|---|
| Test No. | Inhibitor Type | Concentration | Weight Loss (g) | Corrosion Rate (MPY[2]) | Percent Protection |
| 1 | None[4] | 0 | 0.1537 | 56.4 | 0 |
|   | Ex. 1 | 100 ppm[1] | 0.0231 | 8.5 | 85 |
| 2 | None[4] | 0 | 0.1855 | 76.5 | 0 |
|   | Ex. 3 | 100 ppm | 0.0099 | 4.0 | 95 |
|   | Ex. 4 | 100 ppm | 0.0588 | 24.3 | 68 |
| 3 | None[4] | 0 | 0.1220 | 49.3 | 0 |
|   | Ex. 4 | 100 ppm | 0.0211 | 8.6 | 83 |
|   | Ex. 5 | 100 ppm | 0.0227 | 9.3 | 81 |
| 4 | None[4] | 0 | 0.1056 | 40.9 | 0 |
|   | Ex. 6 | 100 ppm | 0.0236 | 9.3 | 78 |
| 5 | None[4] | 0 | 0.1726 | 70.9 | 0 |
|   | Ex. 7 | 100 ppm | 0.0366 | 15.0 | 79 |
|   | Ex. 9 | 100 ppm | 0.0145 | 6.0 | 92 |
| 6 | None[4] | 0 | 0.3290 | 134.8 | 0 |
|   | Ex. 10 | 100 ppm | 0.0627 | 25.6 | 81 |
| 7 | None[4] | 0 | 0.3328 | 131.0 | 0 |
|   | CORBAN A-163[3] | 100 ppm | 0.0658 | 26.0 | 80 |

[1]ppm is parts per million by weight
[2]MPY is mils per year
[3]CORBAN A-163 is a commercial corrosion inhibitor available from Dowell-Schlumberger
[4]Not an example of the present invention The data in Table I demonstrates that the inhibitors of this invention exhibit good corrosion protection under simulated down hole tests at 175° F. In most cases, the corrosion protection is better or comparable to that exhibited by commercially available Corban A-163. Thus, the corrosion inhibitors of this invention are suitable for the protection of metal alloys against corrosion due to the corrosive fluids produced in oil and gas wells at temperatures at or below 175° F. In addition, the corrosion inhibitors of this invention are suitable for the corrosion protection of pipelines, storage tanks, pumps, etc. that exist above ground for the purpose of separating, recovering, and/or transporting the oil and/or gas from the produced fluids.

EXAMPLE 12

The following example demonstrates the performance of the inhibitors of this invention in a 350° F. (177° C.) wheel test. The concentrations and results are given in Table II.

TABLE II

| | 177° C. Wheel Test | | | |
|---|---|---|---|---|
| Test No. | Inhibitors Type | Concentration | Weight Loss (g) | Percent Protection |
| 1 | None[2] | 0 | 0.1192 | 0 |
| 2 | Ex. 2 | 100 ppm[1] | 0.0806 | 33 |
| 3 | Ex. 3 | 100 ppm | 0.0809 | 33 |

TABLE II-continued

| | 177° C. Wheel Test | | | |
|---|---|---|---|---|
| Test No. | Inhibitors Type | Concentration | Weight Loss (g) | Percent Protection |
| 4 | Ex. 5 | 100 ppm | 0.0794 | 34 |

[1]ppm is parts per million parts by weight
[2]Not an example of the present invention The above data shows that the inhibitors of this invention provide some corrosion protection at 177° C. (350° F.) demonstrating the value of these inhibitors for high temperature and high pressure oil and gas well down hole environments.

I claim:

1. A new composition of matter which comprises the reaction product of
    (A) at least one aromatic heterocyclic material having one or more rings, at least two nitrogen atoms and at least one substituent group which has at least one reactive hydrogen atom attached to a carbon atom which is attached to an aromatic heterocyclic ring selected from the group consisting of pyrazines, pyrazoles, imidazoles, pyridazines, pyrimidines, purines, pteridines, triazines, quinoxalines and mixtures thereof; and
    (B) at least one saturated or unsaturated aliphatic or cycloaliphatic monoaldehyde having at least six carbon atoms or ketone having at least six carbon atoms or a combination thereof; and
wherein components (A) and (B) are employed in a molar ratio of (A) to (B) of from about 0.2:1 to about 5:1.

2. A composition of claim 1 wherein component (A) is a pyrazine, pyridazine, pyrimidine, quinoxaline or a mixture thereof and components (A) and (B) are employed in a molar ratio of (A) to (B) of from about 0.75:1 to about 1.5:1.

3. A composition of claim 2 wherein component (A) is 2,5-dimethylpyrazine, 2,3,5,6-tetramethylpyrazine or mixture thereof; component (B) is dodecanal, tetradecanal, hexadecanal, heptadecanal, octadecanal, nonadecanal, 2-methylundecanal, trans,trans-2,4-nonadienal, 3,6-octadecadienal, 9,12-octadecadienal, 6,9,12-octadecatrienal or mixture thereof; and components (A) and (B) are employed in a molar ratio of (A) to (B) of from about 0.9:1 to about 1.5:1.

4. A process for preventing or reducing the corrosion of a metal composition in contact with corrosive fluids which process comprises contacting the surface of said metal composition with an effective amount of a corrosion inhibiting composition of claim 1.

5. A process of claim 4 wherein the corrosion inhibitor is present in an amount of from about 5 to about 2000 ppm by weight of the corrosive flud in contact with the metal composition.

6. A process for preventing or reducing the corrosion of a metal composition in contact with corrosive fluids which process comprises contacting the surface of said metal composition with an effective amount of a corrosion inhibiting composition of claim 2.

7. A process of claim 6 wherein the corrosion inhibitor is present in an amount of from about 5 to about 2000 ppm by weight of the corrosive fluid in contact with the metal composition.

8. A process for preventing or reducing the corrosion of a metal composition in contact with corrosive fluids which process comprises contacting the surface of said metal composition with an effective amount of a corrosion inhibiting composition of claim 3.

9. A process of claim 8 wherein the corrosion inhibitor is present in an amount of from about 5 to about 2000 ppm by weight of the corrosive fluid in contact with the metal composition.

10. A new composition of matter which comprises the reaction product of
    (A) at least one aromatic heterocyclic material having one or more rings, at least one nitrogen atom and at least one substituent group which has at least one reactive hydrogen atom attched to a carbon atom which is attached to an aromatic heterocyclic ring; and
    (B) at least one saturated or unsaturated aliphatic or cycloaliphatic ketone or mixture of aldehyde and ketone having at least six carbon atoms; and
wherein components (A) and (B) are employed in a molar ratio of (A) to (B) of from about 0.2:1 to about 5:1.

11. A composition of claim 10 wherein component (A) is a pyridine, pyrazine, quinoline, quinoxaline or a mixture thereof and components (A) and (B) are employed in a molar ratio of (A) to (B) of from about 0.75:1 to about 1.5:1.

12. A composition of claim 11 wherein component (A) is 2,4-dimethylpyridine, 2,4,6-trimethylpyridine, 2,5-dimethylpyrazine, 2,3,5,6-tetramethylpyrazine or mixture thereof; component (B) is 2-undecanone, 5,7-dimethyl-3,5,9-decatrien-2-one or mixture thereof; and components (A) and (B) are employed in a molar ratio of (A) to (B) of from about 0.9:1 to about 1.5:1.

13. A process for preventing or reducing the corrosion of a metal composition in contact with corrosive fluids which process comprises contacting the surface of said metal composition with an effective amount of a corrosion inhibiting composition of claim 10.

14. A process of claim 13 wherein the corrosion inhibitor is present in an amount of from about 5 to about 2000 ppm by weight of the corrosive fluid in contact with the metal composition.

15. A process for preventing or reducing the corrosion of a metal composition in contact with corrosive fluids which process comprises contacting the surface of said metal composition with an effective amount of a corrosion inhibiting composition of claim 11.

16. A process of claim 15 wherein the corrosion inhibitor is present in an amount of from about 5 to about 2000 ppm by weight of the corrosive fluid in contact with the metal composition.

17. A process for preventing or reducing the corrosion of a metal composition in contact with corrosive fluids which process comprises contacting the surface of said metal composition with an effective amount of a corrosion inhibiting composition of claim 12.

18. A process of claim 17 wherein the corrosion inhibitor is present in an amount of from about 5 to about 2000 ppm by weight of the corrosive fluid in contact with the metal composition.

19. A process for preventing the corrosion of a metal composition in contact with corrosive fluids, which process comprises contacting the surface of said metal composition with an effective amount of, as a corrosion inhibitor, a composition which comprises the reaction product of
    (A) at least one pyridine or quinoline having at least one substituent group which has at least one reactive hydrogen atom attached to a carbon atom which is attached to the pyridine or quinoline ring; and (B) at least one saturated or unsaturated aliphatic or cycloaliphatic monoaldehyde; and wherein components (A) and (B) are employed in a molar ratio of (A) to (B) of from about 0.2:1 to about 5:1.

20. A process of claim 19 wherein component (A) is 2,4-dimethylpyridine, 2,6-dimethylpyridine, 2,4,6-trimethylpyridine or combination of such materials; and component (B) is dodecanal, tetradecanal, hexadecanal, heptadecanal, octadecanal, nonadecanal, 2-methylundecanal, trans,trans-2,4-nonadienal, 3,6-octadecadienal, 9,12-octadecadienal, 6,9,12-octadecatrienal or mixture thereof; and components (A) and (B) are employed in a molar ratio of (A) to (B) of from about 0.75:1 to about 1.5:1.

21. A process of claim 19 wherein the corrosion inhibitor is present in an amount of from about 5 to about 2000 ppm by weight of the corrosive fluid in contact with the metal composition.

22. A process of claim 20 wherein the corrosion inhibitor is present in an amount of from about 5 to about 2000 ppm by weight of the corrosive fluid in contact with the metal composition.

23. A process for preventing the corrosion of a metal composition in contact with corrosive fluids, which process comprises contacting the surface of said metal composition with an effective amount of, as a corrosion inhibitor, a composition which comprises the reaction product of (A) at least one aromatic heterocyclic material having one or more rings, at least one nitrogen atom and at least one substituent group which has at least one reactive hydrogen atom attached to a carbon atom which is attached to an aromatic heterocyclic ring selected from the group consisting of pyridine pyrazines, pyrazoles, imidazoles, pyridazines, pyrimidines, purines, pteridines, triazines, quinoxalines and mixtures thereof; and (B) at least one aromatic, aryl substituted aliphatic or aliphatic substituted aromatic monoaldehyde, ketone or their mixture; and wherein components (A) and (B) are employed in a molar ratio of (A) to (B) of from about 0.2:1 to about 5:1.

24. A process of claim 23 wherein component (A) is a pyridine, pyrazine, quinoline, quinoxaline or a mixture thereof and components (A) and (B) are employed in a molar ratio of (A) to (B) of from about 0.75:1 to about 1.5:1.

25. A process of claim 24 wherein component (A) is 2,5-dimethylpyrazine, 2,3,5,6-tetramethylpyrazine or mixture thereof; and component (B) is trans-cinnamaldehyde; and components (A) and (B) are employed in a molar ratio of (A) to (B) of from about 0.9:1 to about 1.5:1.

26. A process of claim 23 wherein the corrosion inhibitor is present in an amount of from about 5 to about 2000 ppm by weight of the corrosive fluid in contact with the metal composition.

27. A process of claim 24 wherein the corrosion inhibitor is present in an amount of from about 5 to about 2000 ppm by weight of the corrosive fluid in contact with the metal composition.

28. A process of claim 25 wherein the corrosion inhibitor is present in an amount of from about 2000 ppm by weight of the corrosive fluid in contact with the metal composition.

29. A corrosion inhibiting composition comprising (A) from about 10 to about 99 percent by weight of a carrier liquid and (B) from about 1 to about 90 percent by weight of a corrosion inhibitor which is the product which results from reacting (1) at least one material having one or more rings, at least one nitrogen atom and at least one substituent group which has at least one reactive hydrogen atom which is attached to a carbon atom which is attached to an aromatic heterocyclic ring selected from the group consisting of pyridine pyrazines, pyrazoles, imidazoles, pyridazines, pyrimidines, purines, pteridines, triazines, quinoxalines and mixtures thereof; with (2) a monoaldehyde, ketone or mixture of monoaldehyde or ketone wherein components (1) and (2) are employed in a molar ratio of (1) and (2) are employed in a molar ratio of (1) to (2) of from about 0.2:1 to about 5:1.

30. A corrosion inhibiting composition of claim 29 wherein component (1) is a pyridine, pyrazine, quinoxaline or a mixture thereof and components (1) and (2) are employed in a molar ratio of (1) to (2) of from about 0.72:1 to about 1.5:1; component (A) is present in an amount of from about 30 to about 90 percent by weight and component (B) is present in an amount of from about 10 to about 70 percent by weight.

31. A corrosion inhibiting composition of claim 29 wherein component (1) is 2,4,6-trimethylpyridine, 2,5-dimethylpyrazine, 2,3,5,6-tetramethylpyrazine or mixture thereof; component (2) is dodecanal, tetradecanal, hexadecanal, heptadecanal, octadecanal, nonadecanal, 2-methylundecanal, trans,trans-2,4-nonadienal, 3,6-octadecadienal, 9,12-octadecadienal, 6,9,12-octadecatrienal or mixture thereof; components (1) and (2) are employed in a molar ratio of (1) to (2) of from about 0.9:1 to about 1.5:1; component (A) is present in an amount of from about 60 to about 90 percent by weight and component (B) is present in an amount of from about 10 to about 40 percent by weight.

32. A process for preventing or reducing the corrosion of a metal composition in contact with corrosive fluids which process comprises contacting the surface of said metal composition with an effective amount of a corrosion inhibiting composition of claim 29.

33. A process of claim 32 wherein the corrosion inhibitor is present in an amount of from about 5 to about 2000 ppm by weight of the corrosive fluid in contact with the metal composition.

34. A process for preventing or reducing the corrosion of a metal composition in contact with corrosive fluids which process comprises contacting the surface of said metal composition with an effective amount of a corrosion inhibiting composition of claim 30.

35. A process of claim 34 wherein the corrosion inhibitor is present in an amount of from about 5 to about 2000 ppm by weight of the corrosive fluid in contact with the metal composition.

36. A process for preventing or reducing the corrosion of a metal composition in contact with corrosive fluids which process comprises contacting the surface of said metal composition with an effective amount of a corrosion inhibiting composition of claim 31.

37. A process of claim 36 wherein the corrosion inhibitor is present in an amount of from about 5 to about 2000 ppm by weight of the corrosive fluid in contact with the metal composition.

* * * * *

UNITED STATES PATENT AND TRADEMARK OFFICE
CERTIFICATE OF CORRECTION

PATENT NO. : 4,676,834

DATED : June 30, 1987

INVENTOR(S) : Duane S. Treybig

It is certified that error appears in the above-identified patent and that said Letters Patent is hereby corrected as shown below:

Under "OTHER PUBLICATIONS", 2nd Column, 1st line; change "α-Styrylpyridine²" to --α-Styrylpyridine"--.

Col. 5, line 59; change "3-pehnyl-" to --3-phenyl- --.

Col. 6, line 45; change "8-nonadecan-" to --8-nonadecen- --.

Col. 6, line 48; change "11-eicosen-3one," to --11-eicosen-3-one,--.

Col. 11, line 36; change "weighted" to --weighed--.

Col. 13, line 55, Claim 5; change "flud" to --fluid--.

Col. 16, line 21, Claim 30; insert --quinoline,-- after "pyrazine,".

Col. 16, line 24, Claim 30; change "0.72:1" to --0.75:1--.

Signed and Sealed this

Twenty-sixth Day of April, 1988

Attest:

DONALD J. QUIGG

Attesting Officer        Commissioner of Patents and Trademarks